United States Patent
Knighton et al.

(10) Patent No.: US 12,376,762 B2
(45) Date of Patent: Aug. 5, 2025

(54) CARDIAC TISSUE CHARACTERIZATION USING CATHETERIZED LIGHT SCATTERING SPECTROSCOPY

(71) Applicant: UNIVERSITY OF UTAH RESEARCH FOUNDATION, Salt Lake City, UT (US)

(72) Inventors: Nathan J. Knighton, Syracuse, UT (US); Robert W. Hitchcock, Salt Lake City, UT (US); Frank B. Sachse, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 435 days.

(21) Appl. No.: 17/786,484

(22) PCT Filed: Dec. 17, 2020

(86) PCT No.: PCT/US2020/065648
§ 371 (c)(1),
(2) Date: Jun. 16, 2022

(87) PCT Pub. No.: WO2021/127204
PCT Pub. Date: Jun. 24, 2021

(65) Prior Publication Data
US 2023/0033444 A1    Feb. 2, 2023

Related U.S. Application Data

(60) Provisional application No. 62/949,290, filed on Dec. 17, 2019.

(51) Int. Cl.
*A61B 5/06* (2006.01)
*A61B 1/00* (2006.01)

(52) U.S. Cl.
CPC ............ *A61B 5/061* (2013.01); *A61B 1/0008* (2013.01)

(58) Field of Classification Search
CPC ............................. A61B 5/061; A61B 1/0008
(Continued)

(56) References Cited

U.S. PATENT DOCUMENTS

| 5,429,131 A | 7/1995 | Scheinman et al. |
| 5,687,737 A | 11/1997 | Branham et al. |

(Continued)

FOREIGN PATENT DOCUMENTS

| CN | 101453942 A | 6/2009 |
| CN | 103747756 A | 4/2014 |

(Continued)

OTHER PUBLICATIONS

Diaz et al., "Spectral classifier design with ensemble classifiers and misclassification-rejection: application to elastic-scattering spectroscopy for detection of colonic neoplasia", Journal of biomedical optics., 16.6 (2011), 067009.

(Continued)

*Primary Examiner* — Nadia A Mahmood
(74) *Attorney, Agent, or Firm* — Workman Nydegger

(57) ABSTRACT

Disclosed are devices, systems, and methods for characterizing tissue using light scattering spectroscopy. A tissue characterization probe includes an elongate member having a proximal end and a plurality of distal probe tips at a distal end. A plurality of illumination fibers extend through the elongate member to the distal probe tips such that each distal probe tip includes at least one illumination fiber. A plurality of detection fibers also extend through the elongate member such that each probe tip includes at least one detection fiber. The disclosed devices and systems beneficially enable characterization of tissues within depths greater than 100 μm.

(Continued)

The disclosed devices and systems also enable effective characterization of anisotropic tissues, such as cardiac myocardium.

44 Claims, 6 Drawing Sheets

(58) Field of Classification Search
USPC .......................................................... 600/300
See application file for complete search history.

(56) References Cited

U.S. PATENT DOCUMENTS

| | | | |
|---|---|---|---|
| 6,004,269 A | 12/1999 | Crowley et al. | |
| 6,228,082 B1 | 5/2001 | Baker et al. | |
| 7,001,383 B2 | 2/2006 | Keidar | |
| 7,499,153 B2 | 3/2009 | Puppels et al. | |
| 8,029,766 B2 | 10/2011 | Elmaleh et al. | |
| 8,059,274 B2 | 11/2011 | Splinter | |
| 8,106,905 B2 | 1/2012 | Markowitz et al. | |
| 8,316,861 B2 | 11/2012 | Brewer et al. | |
| 8,432,542 B2 | 4/2013 | Marple et al. | |
| 8,496,579 B2 | 7/2013 | Koenig et al. | |
| 8,876,815 B2 | 11/2014 | Coe et al. | |
| 9,763,642 B2 | 9/2017 | Harks et al. | |
| 10,143,398 B2 | 12/2018 | Altmann et al. | |
| 10,231,706 B2 | 3/2019 | Chen et al. | |
| 11,154,186 B2 | 10/2021 | Sachse et al. | |
| 2004/0054366 A1 | 3/2004 | Davison et al. | |
| 2004/0092806 A1 | 5/2004 | Sagon et al. | |
| 2004/0092846 A1 | 5/2004 | Watrous | |
| 2004/0153057 A1 | 8/2004 | Davison | |
| 2004/0254474 A1 | 12/2004 | Seibel et al. | |
| 2005/0033135 A1 | 2/2005 | Govari | |
| 2005/0148836 A1 | 7/2005 | Kleen et al. | |
| 2005/0242298 A1 | 11/2005 | Genet et al. | |
| 2005/0288665 A1 | 12/2005 | Woloszko | |
| 2006/0041199 A1 | 2/2006 | Elmaleh et al. | |
| 2006/0229515 A1 | 10/2006 | Sharareh et al. | |
| 2006/0253031 A1 | 11/2006 | Altmann et al. | |
| 2007/0038123 A1 | 2/2007 | Fulghum | |
| 2007/0179397 A1 | 8/2007 | Hashimshony et al. | |
| 2007/0299352 A1 | 12/2007 | Harlev et al. | |
| 2007/0299353 A1 | 12/2007 | Harlev et al. | |
| 2008/0183036 A1 | 7/2008 | Saadat et al. | |
| 2008/0262359 A1 | 10/2008 | Tearney et al. | |
| 2008/0306391 A1* | 12/2008 | Hular | A61B 5/061 600/478 |
| 2009/0076375 A1 | 3/2009 | Maschke | |
| 2009/0076498 A1 | 3/2009 | Saadat et al. | |
| 2009/0147257 A1 | 6/2009 | Splinter | |
| 2009/0231578 A1* | 9/2009 | Ling | A61B 5/02007 356/301 |
| 2009/0299195 A1* | 12/2009 | Muller | A61B 5/0062 600/478 |
| 2009/0326320 A1 | 12/2009 | Sinofsky et al. | |
| 2010/0092064 A1 | 4/2010 | Li | |
| 2011/0028967 A1 | 2/2011 | Rollins et al. | |
| 2011/0082451 A1 | 4/2011 | Melsky | |
| 2011/0118590 A1 | 5/2011 | Zhang | |
| 2011/0301438 A1 | 12/2011 | Sachse et al. | |
| 2012/0053452 A1 | 3/2012 | Tal | |
| 2012/0075619 A1 | 3/2012 | Nieman et al. | |
| 2012/0108957 A1 | 5/2012 | Desai | |
| 2012/0172724 A1 | 7/2012 | Hill et al. | |
| 2012/0281218 A1 | 11/2012 | Schnitzer et al. | |
| 2012/0302892 A1 | 11/2012 | Lue et al. | |
| 2013/0102862 A1 | 4/2013 | Mercader et al. | |
| 2013/0204134 A1 | 8/2013 | Harks et al. | |
| 2013/0218019 A1 | 8/2013 | Abraham | |
| 2013/0315455 A1 | 11/2013 | Wakai | |
| 2014/0018792 A1 | 1/2014 | Gang et al. | |
| 2014/0031802 A1 | 1/2014 | Melsky et al. | |
| 2014/0058246 A1 | 2/2014 | Boveja et al. | |
| 2014/0081113 A1 | 3/2014 | Cohen et al. | |
| 2014/0088418 A1 | 3/2014 | Radulescu et al. | |
| 2014/0171942 A1 | 6/2014 | Werneth et al. | |
| 2015/0011843 A1 | 1/2015 | Toth et al. | |
| 2015/0119708 A1 | 4/2015 | Sachse et al. | |
| 2015/0182282 A1 | 7/2015 | Zemel et al. | |
| 2015/0351722 A1 | 12/2015 | Chen et al. | |
| 2016/0228180 A1 | 8/2016 | Sliwa et al. | |
| 2017/0027503 A1 | 2/2017 | Sachse et al. | |
| 2017/0061617 A1 | 3/2017 | Cochet et al. | |
| 2017/0251963 A1 | 9/2017 | Hashimoto et al. | |
| 2018/0103852 A1 | 4/2018 | Dagdeviren et al. | |
| 2019/0223706 A1 | 7/2019 | Takeuchi et al. | |
| 2020/0022573 A1 | 1/2020 | Sachse et al. | |
| 2020/0246497 A1 | 8/2020 | Hara et al. | |

FOREIGN PATENT DOCUMENTS

| | | |
|---|---|---|
| CN | 105163651 A | 12/2015 |
| EP | 2712546 A1 | 4/2014 |
| JP | 2004-160212 A | 6/2004 |
| JP | 2005-152654 A | 6/2005 |
| JP | 2008-504557 A | 2/2008 |
| JP | 2009-539566 A | 11/2009 |
| JP | 2012-505028 A | 3/2012 |
| JP | 2012-196437 A | 10/2012 |
| JP | 2016-536065 A | 11/2016 |
| JP | 2017-153876 A | 9/2017 |
| JP | 2019-076621 A | 5/2019 |
| JP | 2019-130155 A | 8/2019 |
| JP | 2019-171021 A | 10/2019 |
| WO | 2006/020920 A2 | 2/2006 |
| WO | 2007/146864 A3 | 12/2008 |
| WO | 2014/028584 A1 | 2/2014 |
| WO | 2014/165990 A1 | 10/2014 |
| WO | 2015/073932 A1 | 5/2015 |
| WO | 2015/165978 A1 | 11/2015 |
| WO | 2016/181318 A1 | 11/2016 |
| WO | 2016/205731 A1 | 12/2016 |
| WO | 2018/144648 A1 | 8/2018 |

OTHER PUBLICATIONS

Femnou et al., "Intra-cardiac Side-Firing Light Catheter for Monitoring Cellular Metabolism using Transmural Absorbance Spectroscopy of Perfused Mammalian Hearts", JoVE (Journal of Visualized Experiments), 147 (2019):e58992.

Final Office Action received for U.S. Appl. No. 15/222,858, mailed on Aug. 11, 2020, 13 pages.

Final Office Action received for U.S. Appl. No. 16/482,389, mailed on Nov. 22, 2021, 18 pages.

Final Office Action received for U.S. Appl. No. 15/222,858, mailed on Nov. 15, 2019.

International Search Report and Written Opinion for PCT/US2016/044845 mailed Oct. 7, 2016.

International Search Report and Written Opinion issued in PCT/US2018/016314 dated Mar. 12, 2018.

International Search Report and Written Opinion received for PCT Patent Application No. PCT/US2020/065648, mailed on May 7, 2021, 12 pages.

Knighton et al., "Towards Cardiac Tissue Characterization Using Machine Learning and Light-Scattering Spectroscopy," USA, 84112, 2015, 26 pages.

Knighton et al., "Towards Intraoperative Quantification of Atrial Fibrosis Using Light Scattering Spectroscopy and Convolutional Neural Networks," UT 84112, USA, 16 pages.

Non-Final Office Action received for U.S. Appl. No. 15/222,858, mailed on Jan. 4, 2021, 13 pages.

Non-Final Office Action received for U.S. Appl. No. 16/482,389, mailed on Aug. 17, 2021, 21 pages.

Non-Final Office Action received for U.S. Appl. No. 16/482,389, mailed on May 5, 2022, 20 pages.

Office Action received for U.S. Appl. No. 15/222,858, mailed on Jan. 23, 2020.

Office Action received for U.S. Appl. No. 15/222,858, mailed on Feb. 28, 2019.

(56) References Cited

OTHER PUBLICATIONS

Rajitha et al., "Machine learning classification of human joint tissue from diffuse reflectance spectroscopy data", Biomedical optics express, 10.8 (2019): 3889-3898.

* cited by examiner

CARDIAC TISSUE CHARACTERIZATION USING CATHETERIZED LIGHT SCATTERING SPECTROSCOPY

CROSS-REFERENCE TO RELATED APPLICATIONS

This patent application is a nationalization of and claims priority to PCT Application No. PCT/US2020/065648 filed on Dec. 17, 2020 and titled "Cardiac Tissue Characterization Using Catheterized Light Scattering Spectroscopy", which claims priority to and the benefit of U.S. Provisional Patent Application No. 62/949,290, filed Dec. 17, 2019 and titled "Cardiac Tissue Characterization Using Catheterized Light Scattering Spectroscopy". Each of the aforementioned applications is incorporated by reference herein in their entirety.

STATEMENT REGARDING FEDERALLY SPONSORED RESEARCH

This invention was made with government support under grant nos. HL128813 and HL135077 awarded by the National Institutes of Health. The government has certain rights in the invention.

BACKGROUND

Cardiac diseases cause significant disease burden in society. Abnormal cardiac tissue microstructure is often associated with cardiac disease. Cardiac diseases associated with microarchitectural abnormalities include allograft rejection, myocarditis, amyloidosis, hypertrophy, and other cardiomyopathies.

One particular type of this remodeling is fibrosis, which occurs as a maladaptive response to metabolic, hemodynamic, and ischemic stresses. Fibrosis is defined as the excessive formation of connective tissue comprising, in particular, extracellular matrix, fibroblasts and myofibroblasts. During development of fibrosis, extracellular matrix proteins including collagen-1 and fibronectin-1 are excessively produced and released into atrial tissues. Fibrosis significantly alters the mechanical properties of cardiac tissues. One effect is that fibrosis reduces myocardial mechanical function as quantified, e.g., by radial strain and ejection fraction.

Important examples of cardiac diseases associated with fibrosis are myocardial infarction and atrial fibrillation (AF). In myocardial infarction muscle tissues is replaced with fibrotic tissue, which can cause arrhythmia. Fibrosis is also thought to maintain arrhythmia such as AF. Typical AF treatment involves rate control using drugs, such as beta blockers, and anticoagulation to prevent thromboembolism. However, for patients who remain symptomatic, rhythm control with antiarrhythmic medications and/or transcatheter ablation are commonly chosen treatment options. Catheter ablation involves selectively destroying tissue regions, a process usually achieved by applying radio frequency ("RF") energy to heat the tissue. Several trials have suggested that catheter ablation can lead to maintained long-term sinus rhythm in AF patients. Nevertheless, the recurrence rate of AF after ablation is as high as 50%. Additionally, 20-40% of AF patients will undergo multiple ablation procedures.

Other important examples for cardiac diseases are characterized by changes in the density of cells and their nuclei due to infiltration and proliferation. These examples include myocarditis and allograft rejection. Similarly, cardiac hypertrophy is characterized by a change in the density of the cardiac muscle cells.

Diagnosis and/or treatment of cardiac diseases associated with microstructure abnormalities (such as AF, allograft rejection, myocarditis, hypertrophy, and amyloidosis) could potentially be enhanced if cardiac tissue characterization and mapping could be improved. Unfortunately, conventional methods for identifying and diagnosing cardiac tissues have not been able to provide effective characterization.

Macroscopic regions of cardiac tissue can be visualized using magnetic resonance imaging (MRI), for instance, late gadolinium enhanced MRI. However, not all care centers have access to the requisite and relatively expensive MRI equipment, and such procedures are associated with high costs. Further, while MRI imaging may detect certain tissue abnormalities at the macroscopic scale, it has limited resolution and does not provide insights into the microscopic distribution and composition of microarchitectural abnormalities.

Fiber-optics confocal microscopy (FCM) may be utilized as an optical approach for imaging cardiac tissues. However, suitable FCM systems require expensive hardware. Further, FCM has limited depth penetration and is therefore unable to provide information about tissues of interest that are deeper than about 100 μm.

An established clinical tool for assessment of cardiac tissue microstructure is endomyocardial biopsy (EMB), which requires an invasive procedure for tissue extraction. Further, the procedure is only rarely performed in the atria due to its high complication rate.

Accordingly, there exists a long felt and ongoing need for devices and methods capable of characterizing cardiac tissue at relevant tissue depths and at the microstructure scale. Such advances will beneficially improve outcomes and reduce disease burden.

BRIEF SUMMARY

In one embodiment, a tissue characterization probe includes an elongate member having a proximal end and a plurality of distal probe tips disposed at or near the distal end of the elongate member to form a multi-arm arrangement. A plurality of illumination fibers extend at least partially through the elongate member, each extending to a respective probe tip of the multi-arm arrangement such that each probe tip includes at least one illumination fiber. A plurality of detection fibers also extend at least partially through the elongate member so that each probe tip of the multi-arm arrangement includes at least one detection fiber, and optionally multiple detection fibers.

In one embodiment, a tissue characterization probe includes an elongate member having a proximal end and a distal probe tip at a distal end. An illumination fiber extends through the elongate member to the distal probe tip and is configured to pass light to and beyond the probe tip into targeted tissue. A plurality of detection fibers also extend through the elongate member to the probe tip and are configured to receive light scattered from the targeted tissue.

The detection fibers are arranged relative to the illumination fiber in a manner that beneficially enables characterization of tissues within depths greater than 100 μm, such us up to about 4 mm, or up to about 8 mm, or up to about 12 mm, or up to about 16 mm, or up to about 20 mm, or up to about 25 mm, or up to about 30 mm. The detection fibers are also arranged to enable effective characterization of anisotropic tissues, such as myocardium.

In one embodiment, a first set of detection fibers is disposed along a first detection line, the first detection line being orthogonal to the illumination axis. A second set of detection fibers is disposed along a second detection line. The second detection line is transverse to the first detection line, preferably orthogonal to the first detection line. The first and second sets of detection fibers preferably each have at least two detection fibers.

In one embodiment, a method of characterizing tissue includes the steps of: (i) providing a tissue characterization system; (ii) directing the distal probe tip of the tissue characterization system to a targeted anatomical location; (iii) at the targeted anatomical location, operating the tissue characterization probe to obtain spectroscopic data at depths greater than about 100 μm (such as up to about 1 mm, or up to about 1.5 mm, or up to about 2 mm, or up to about 2.5 mm, or up to about 3 mm, or up to about 3.5 mm, or up to about 4 mm, or up to about 5 mm, or up to about 7.5 mm, or up to about 10 mm, or up to about 15 mm, or up to about 20 mm, or up to about 25 mm, or up to about 30 mm); and resolving the spectroscopic data in order to characterize the targeted tissue.

The targeted tissue can be cardiac tissue. Methods described herein are particularly applicable to characterizing cardiac tissue within a blood-filled, beating heart. Characterizing the targeted tissue may include detecting, measuring, or monitoring one or more of fibrotic tissue, allograft acceptance or rejection, myocarditis, amyloidosis, other cardiomyopathy, or one or more tissue parameters such as nuclear density. A method may include determining a volume fraction of constituents of targeted tissue and/or spatial distribution of the targeted tissue within the heart.

In the methods described herein, the step of resolving spectroscopic data in order to characterize the targeted tissue may include the use of one or more machine learning techniques. The machine learning technique(s) can include supervised and/or unsupervised techniques.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

DETAILED DESCRIPTION

Introduction

The present disclosure relates to devices, systems, and methods for characterizing tissue, and in particular cardiac tissue, using LSS. The embodiments described herein, including the probes, systems, and methods, may be combined with and/or utilized in conjunction with the devices, systems, and methods described in PCT/US2018/016314 (published as WO2018144648A1), the entirety of which is incorporated herein by this reference.

For example, the tissue characterization probe components described herein may be added to any of the intravascular devices described in PCT/US2018/016314 to thereby add tissue characterization capabilities to the imaging, localization, treatment (e.g., ablation), and/or electrical mapping functions of the intravascular devices of PCT/US2018/016314. Likewise, the tissue characterization methods described herein may be added to any of the methods of generating and/or rendering tissue maps described in PCT/US2018/016314 to thereby add or augment the effective tissue characterization of the maps.

For example, as described in greater detail below, tissue characterization using LSS in conjunction with the optimized embodiments described herein beneficially enables characterization of tissue within greater depths than possible using conventional methods. This additional and/or more accurate tissue characterization information can therefore enhance tissue maps generated using the embodiments described in the PCT/US2018/016314 (published as WO2018144648A1).

It should also be understood that while many of the examples detailed below relate to the detection of fibrosis in cardiac tissue, the same principles and features may be readily applied to other applications where detection, diagnosis, and/or treatment of abnormal tissue microstructure is warranted. Embodiments may therefore be utilized for monitoring the risk of allograft rejection, in myocarditis, amyloidosis, and other cardiomyopathies. Myocardium nuclear density (ND) is one parameter that may be measured and effectively characterized using the described embodiments in order to provide enhanced insight into cardiac microstructure for the purposes of disease monitoring, diagnosis, and/or treatment.

Figure 1:
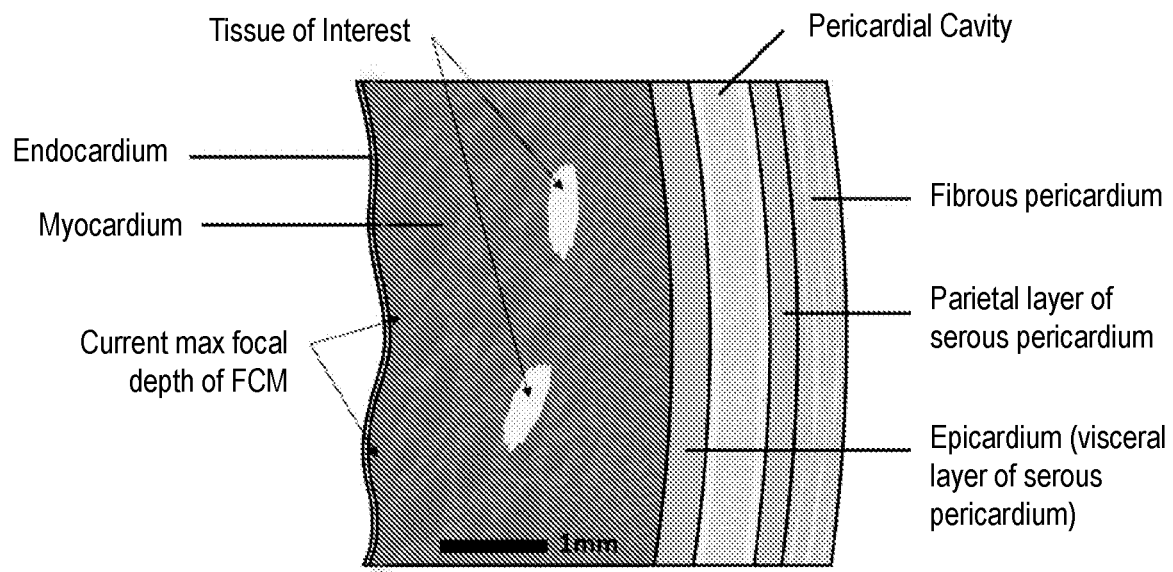
FIG. 1 illustrates a cross-section of the wall of an atrium as an example of a cardiac chamber and visualizes the depth beneath the endocardium surface at which tissues of interest often reside, showing that such tissues of interest often lie beyond the reach of the range for optical imaging.

FIG. 1 illustrates a cross-section of cardiac tissue (e.g., from the atrial wall). As shown, the tissue of interest often lies deeper than the focal depth of FCM. In particular, fibrotic extracellular tissues may reside at depths of about 1 mm or more, whereas conventional optical imaging such as FCM may only have a maximal imaging depth of about 100 μm. Structures and tissues of the cardiac conduction system may also reside at relatively deeper tissue layers.

Moreover, cardiac tissue is comprised of muscle fibers with directionality and anisotropic structure. Such anisotropy can make imaging and characterizing the tissue difficult. For example, even when LSS is used, the scattered light detection signal is affected by the anisotropic arrangement of the targeted cardiac tissue, making accurate characterization of the tissue (e.g., as fibrotic vs. normal) difficult.

Thus, while optical imaging may be sufficient for characterizing surface-level microstructures such as epithelial cells, it is unable to provide information about the underlying tissues. This is a particular disadvantage in cardiac tissue applications, where the tissues of interest very often lie beyond the immediate surface levels. Further, while conventional LSS may in theory be able to provide information about deeper tissue layers, the anisotropic nature of cardiac tissue makes effective characterization elusive.

Tissue Characterization Probes & Systems

Figure 2:
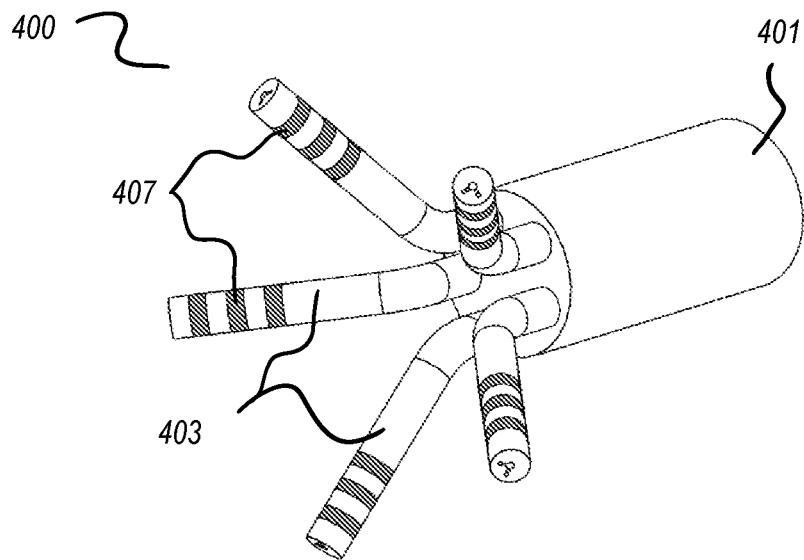
FIG. 2 illustrates an exemplary embodiment of a distal end of a tissue characterization probe having a multi-arm arrangement of distal probe tips.

FIG. 2 illustrates an exemplary embodiment of a tissue characterization probe 400 that includes multiple probe tips 403 disposed in a multi-arm arrangement. The probe 400 includes an elongate member 401 through which illumination fibers and detection fibers may be arranged.

Figure 3A:
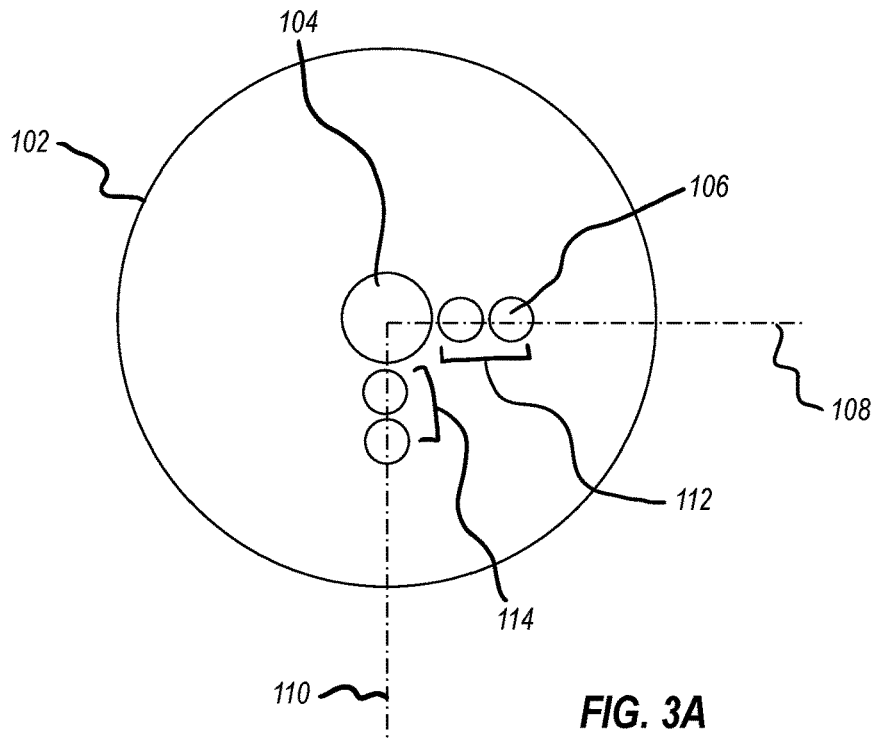
FIGS. 3A through 3C illustrate face views of distal ends of exemplary tissue characterization probes configured to use light scattering spectroscopy (LSS) to characterize cardiac tissue within clinically relevant depths.
Figure 3B:
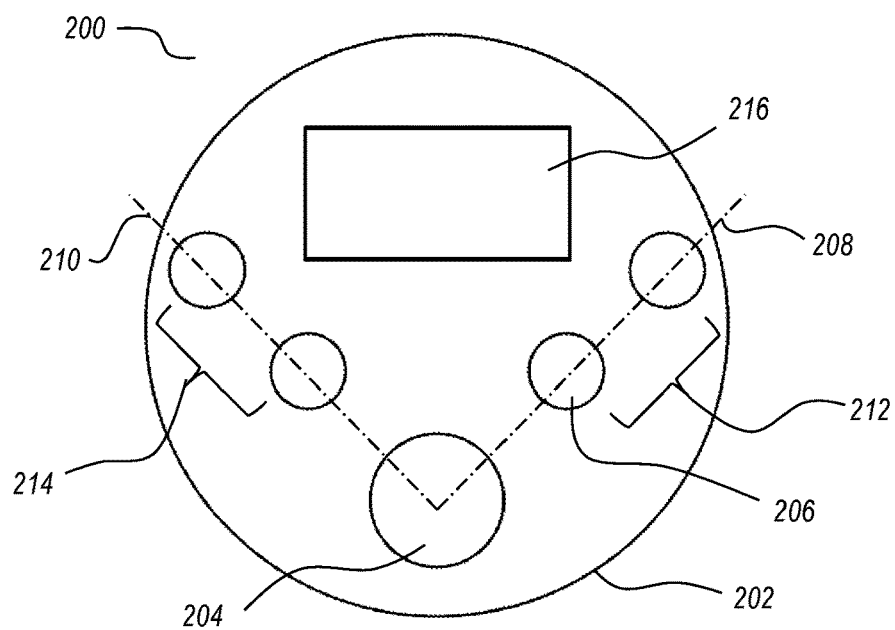
Figure 3C:
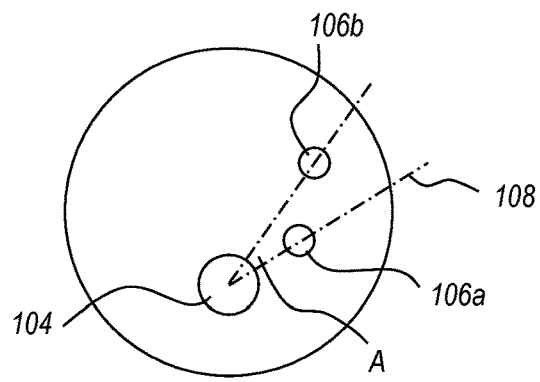
Figure 4:
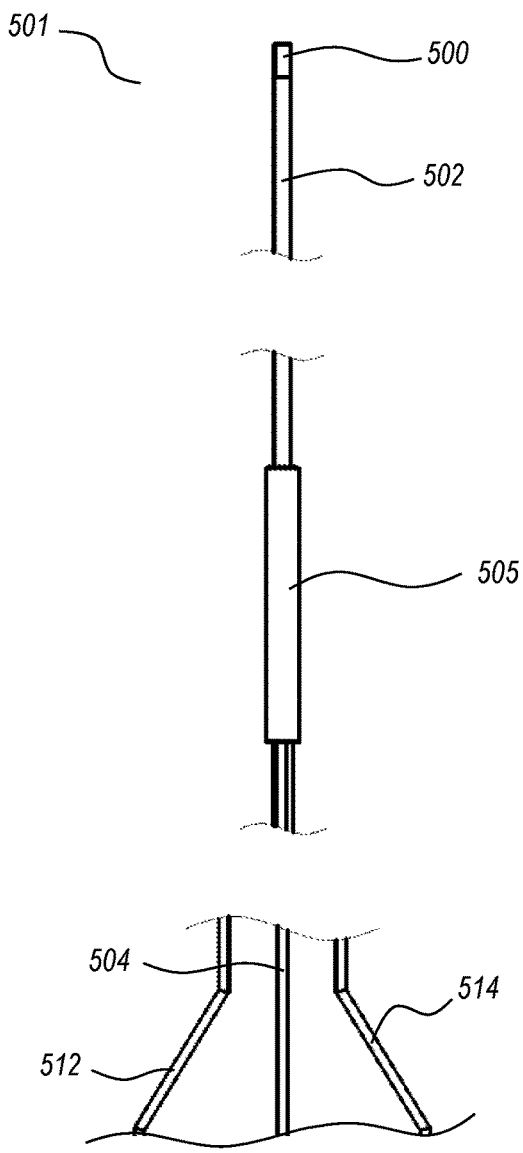
FIG. 4 illustrates an extended view of an exemplary tissue probe assembly.

Each of the probe tips 403 of the multi-arm arrangement may be independently configured according to any of the other probe tip configurations described herein, such as those to be described in greater detail below and which are illustrated in FIGS. 3A through 4. In some embodiments, however, one or more of the probe tips 403 may be configured differently. For example, one or more of the probe tips 403 may include only a single detection fiber and a single illumination fiber. That is, while the overall probe 400 includes multiple detection fibers (e.g., at least one in each separate probe tip 403), each particular probe tip 403 need not necessarily include a plurality of detection fibers.

Further, while particular structural relationships between the illumination fiber and detection fibers are described in relation to the probes of FIGS. 3A through 3C, one or more of the probe tips 403 may have a different configuration, such as by disposing the detection fibers in a radial fashion about the illumination fiber, or disposing the detection fibers along a grid, or disposing the detection fibers in a random orientation relative to the illumination fiber, etcetera.

It will be understood that although the illustrated embodiment includes a particular number of probe tips 403 (i.e., arms), that other embodiments may include more or less arms. In general, a greater number of arms are preferred so long as they may be included within given space and/or cost constraints.

As shown, any of the probe tips 403 may include one or more electrodes 407 configured to provide navigation, mapping, and/or localization functionality. For example, the electrodes 407 may be utilized to determine the location of the probe tip(s) within the three-dimensional anatomical working space so that measurements may be associated with their corresponding locations within the target anatomy. The correlation between location and measurement data can be utilized to generate a three-dimensional map of the target anatomy (e.g., of tissue microstructure of the target anatomy). As shown, the electrodes 407 may be formed as rings. In a preferred embodiment, multiple rings are disposed on the probe tip 403 at different longitudinal locations along the length of the distal section of the probe tip 403. Other embodiments may additionally or alternatively utilize other types of electrodes known in the art.

The multi-arm arrangement illustrated in FIG. 2 can provide several benefits. In particular, the multi-arm arrangement allows for more rapid characterization and mapping of targeted anatomy. This may be particularly important for invasive and/or expensive procedures, such as those involving cardiac catheterization and characterization of cardiac tissues. In addition, the multi-arm arrangement can improve characterization and/or mapping speeds by more than simply a multiple of the number of tips/arms included. For example, the tips/arms of the probe may be positioned at a given location for readings, and the probe may then be rotated to radially reposition the tips/arms for additional readings. In contrast, a single-arm design cannot provide any additional information just through rotation of the probe, and the probe tip must be moved to a new location for each reading.

FIGS. 3A through 3C illustrate face views of distal ends of exemplary tissue characterization probes. configured to provide effective tissue characterization within clinically relevant depths and when characterizing anisotropic tissues such as cardiac tissues. FIG. 3A illustrates a face view of a particular distal probe 100. The distal probe tip may be referred to synonymously herein as "distal tip" or "probe tip".

The probe 100 includes an elongate member 102 forming the outer structure of the device, which may be configured for routing through a patient's vasculature to the heart. An illumination fiber 104 extends through the elongate member 102 and is configured for carrying the source light and passing it beyond the distal end and into the targeted tissue. As shown, a plurality of detection fibers 106 are also disposed within the elongate member 102. The detection fibers 106 are configured to receive the scattered light and pass it back toward the proximal end of the elongate member 102.

The illumination fiber 104 defines an illumination axis of the probe (extending through the paper from the perspective of FIG. 3A). The illumination axis may be substantially centered within the elongate member 102, as in the FIG. 3A embodiment, though other embodiments may position the illumination fiber off the center of the elongate member (as in the FIG. 3B embodiment). A "first detection line" is defined as a line extending orthogonally from the illumination axis, as shown by line 108. A "second detection line" is also defined as a line extending orthogonally from the illumination axis, as shown by line 110.

The first detection line 108 and the second detection line 110 are transverse to one another (i.e., are non-parallel to one another), preferably orthogonal to one another (i.e., perpendicular), as shown. From the cross-sectional view looking along the illumination axis as in FIG. 3A, the first detection line 108 and second detection line 110 may cross each other at the illumination axis to form a transverse angle, such as about 30° to about 150°, or about 60° to about 120°, or preferably about 90°.

A first set 112 of detection fibers is substantially arranged along the first detection line 108, and a second set 114 of detection fibers is substantially arranged along the second detection line 110. Arranging the detection fibers 106 in this manner has been found to provide effective functionality, an in particular has been found to be effective for characterizing cardiac tissue, including anisotropic tissue, within clinically relevant depths.

As used herein, the detection fibers are considered "substantially arranged", "substantially aligned", and/or "substantially disposed" along respective first or second detection lines if they are radially offset from the detection line by no more than about 30 degrees, or no more than about 25 degrees, or no more than about 20 degrees, or no more than about 15 degrees, or no more than about 10 degrees, or no more than about 5 degrees. This is best illustrated with reference to FIG. 3C. If detection line 108 is defined as starting from the illumination fiber 104 and extending across one of the detection fibers (106a, in this case), any other detection fibers in that set of detection fibers should be close to detection line 108, but need not be exactly aligned with it. For example, detection fiber 106b is not aligned exactly with the detection line 108 but is radially offset by an angle "A" from the detection line 108, with the illumination fiber 104 defining the vertex.

Referring again to FIG. 3A, the first set 112 and second set 114 of detection fibers each preferably include at least two detection fibers. Providing at least two detection fibers in a set allows for depth sensitivity. Providing a second set of detection fibers that is transversely offset from the first set (i.e., the two sets form a non-parallel, preferably perpendicular angle with respect to each other, with the illumination fiber 104 acting as vertex) has been found to beneficially reduce directional sensitivity of spectra in anisotropic tissues.

For example, arranging the first set 112 and second set 114 of detection fibers in a transverse manner, and in particular in an orthogonal manner, has been found to provide an overall averaging effect when probing anisotropic tissues that allows for effective tissue characterization despite high levels of anisotropy in the targeted tissues. Thus, by having a first set 112 of at least two detection fibers, and a second set 114 of at least two detection fibers that each radially correspond to the fibers of the first set 112, both depth sensitivity and anisotropic sensitivity are achieved.

Note that although four detection fibers 106 are illustrated in this embodiment (two disposed along the first detection line 108 and two disposed along the second detection line 110), other embodiments may include other numbers of detection fibers. As described above, a tissue characterization probe preferably includes at least four detection fibers (two sets of two each disposed along transverse detection lines) in order to provide effective depth sensitivity and anisotropy sensitivity. Additional detection fibers may be arranged along the transverse detection lines and/or at other positions to further increase resolution and/or sensitivity. In some circumstances, however, space constraints may favor a minimum number of detection fibers.

The spacing of the detection fibers 106 along respective detection lines 108 and 110 may be varied. The characterization system can be configured for specific application needs by varying the spacing and arrangement of fibers. For instance, the detection fibers 106 may be spaced apart from the illumination fiber 104 and/or from one another at distances relevant for particular application needs. In one example, it was found that the combination of adjacent (to the illumination fiber 104) and distal detection fibers generates the most accurate results for some applications.

Thus, although spacing of the detection fibers 106 may be varied according to particular application needs, some embodiments minimize spacing such that the detection fibers are substantially adjacent (e.g., within about 135 μm) to the other detection fibers of a set, and such that each set is substantially adjacent (e.g., within about 135 μm) to the illumination fiber 104.

FIG. 3B illustrates another exemplary embodiment of a distal probe 200 having features similar to distal probe 100, except as noted. As with the embodiment of FIG. 3A, the illustrated embodiment includes an elongate member 202, an illumination fiber 204 extending through the elongate member 202, and a plurality of detection fibers 206 arranged in coordination with the illumination fiber 204 to enable LSS using the distal probe 200.

In the illustrated embodiment, the illumination fiber 204 is off-center from the longitudinal axis of the elongate member 202. As with distal probe 100, detection lines 208 and 210 extend from the illumination fiber 204 and detection fibers 206 are substantially aligned thereon, with a first set 212 substantially aligned on detection line 208 and a second set 214 substantially aligned on detection line 210. Note that in this embodiment the detection fibers 206 are spaced apart from one another and are spaced apart from the illumination fiber 204.

As shown, the detection fibers 206 may be spaced substantially equally upon each respective detection line. For example, along the first detection line 208, the space between each of the fibers (including the illumination fiber 204 and detection fibers 206) is substantially equal. The spacing is preferably repeated in a similar fashion on the second detection line 210 so that each of the detection lines space apart respective detection fibers similarly, though other embodiments may include differential spacing.

As shown, by moving the illumination fiber 204 off of the center of the elongate member 202, the internal space of the elongate member 202 is more efficiently utilized, allowing for smaller overall diameters of the elongate member 202 and/or for the utilization of additional components. For example, the illustrated embodiment includes a support wire 216 that extends at least partially through the elongate member 202 and is configured to increase the bending stiffness of the distal tip 200 and/or provide structure to enable the formation of a bent/shaped tip.

The increased stiffness provided by the support wire 216 can beneficially aid in keeping the distal tip 200 in proper position during a procedure. For example, when taking measurements within a blood-filled, beating heart, it can be difficult to keep the device positioned against the targeted tissue without losing contact or sliding out of position. The increased structure and stiffness make it easier for the user to maintain proper position throughout multiple heartbeats without causing injury to tissue or increasing the difficulty of vascular navigation. The support wire 216 also enables the user to "shape" the tip with a desired bend and/or orientation. A bent tip can be beneficial for navigating particular vasculature passageways and/or for providing other desired structural arrangements, such as the circumferentially arranged probe ends shown in FIG. 2.

The support wire 216 may have a quadrilateral cross-sectional shape. A quadrilateral cross-sectional shape can beneficially provide specified bending planes. That is, the bending stiffness of the support wire 216 will be less along directions that align with edges of the cross-sectional shape than along other directions (e.g., directions diagonal of the shape. In some embodiments, as illustrated, the support wire 216 has a rectangular shape. A rectangular cross-sectional shape may be desired in certain instances because it can provide bending planes of different bending stiffness. For example, the bending stiffness will be greater in the direction that aligns with the long axis of the rectangular cross-section than in the direction that aligns with the short axis of the rectangular cross-section.

The support wire 216 may be positioned anywhere within the distal tip 200. Preferably, the support wire 216 is disposed so that its cross-section is on the acute side of the angle formed between detection lines 208 and 210, as in the illustrated embodiment. This position efficiently utilizes space within the distal tip 200 and thus provides more design flexibility, sizing control, and the like.

The tissue characterization probe 200 is therefore similar in structure and function to the tissue characterization probe 100. However, the tissue characterization probe 200 illustrates that the illumination fiber 204 (and thus the illumination axis) does not necessarily need to be aligned to the center axis of the elongate member 202. As shown, by moving the illumination fiber 204 out of center, the internal space of the elongate member 202 is more efficiently utilized, allowing for smaller overall diameters of the elongate member 202.

FIG. 4 illustrates an extended view of a tissue probe assembly 501 that can incorporate any of the tissue catheterization probe components described herein, including one or more of the distal tips 100 and/or 200 of FIGS. 3A and 3B. Also, although only a single distal tip 500 is illustrated, it will be understood that a multi-arm arrangement, as in FIG. 2, may be utilized.

The illustrated probe assembly 501 includes an elongate member 502 extending between a proximal end and a distal end. The distal tip 500 is disposed at the distal end. A combiner 505 receives multiple component parts at its proximal end and positions them in the manner needed for proper function at the distal tip 500. For example, as shown, the combiner 505 may receive one or more illumination fibers 504, and one or more sets 512, 514 of detection fibers. These may in turn be connected to connectors (not shown) that enable connection to the corresponding components of a tissue characterization/LSS system (e.g., light source and spectrometer).

The probe assembly 501 is configured to be introduced (distal end first) through a lumen or working channel of a catheter, sheath, endoscope, or other such intravascular delivery device. The delivery device can be steerable, such as in the form of a guidable catheter or steerable sheath.

Figure 5:
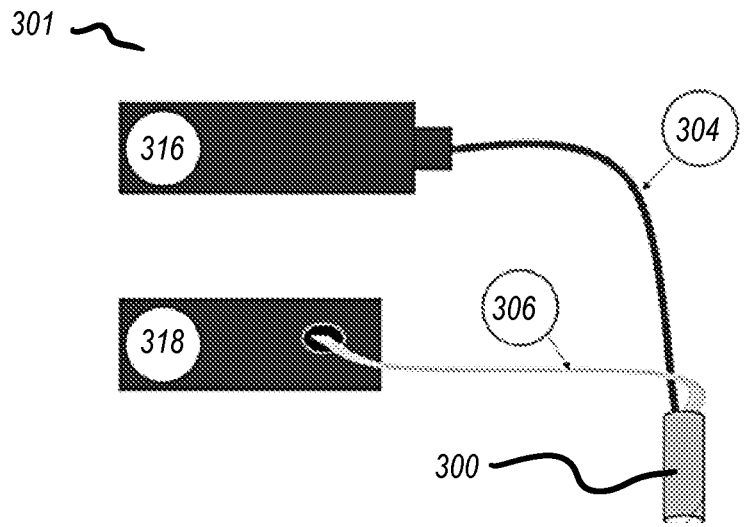
FIG. 5 illustrates an exemplary tissue characterization system that may be utilized for in situ or in vivo characterization of cardiac tissue.

FIG. 5 illustrates one example of a tissue characterization system 301. The system 301 includes a tissue characterization probe 300, which may be configured as the tissue characterization probes 100 and 200 described herein. The illumination fiber 304 extends from the probe 300 and is operatively connected to a suitable light source 316 (e.g., a tungsten-halogen light source or other suitable LSS light source). The detection fibers 306 extend from the probe 300 and are operatively connected to a suitable spectrometer 318 (or multiple spectrometers). Targeted tissue 30 may be characterized using the system 301.

Methods of Characterizing Tissue

In one embodiment, a method of characterizing tissue includes the steps of: (i) providing a tissue characterization system; (ii) directing the distal probe tip of the tissue characterization system to a targeted anatomical location; (iii) at the targeted anatomical location, operating the tissue characterization probe to obtain spectroscopic data at depths greater than about 100 µm (such as up to about 1 mm, or up to about 1.5 mm, or up to about 2 mm, or up to about 2.5 mm, or up to about 3 mm, or up to about 3.5 mm, or up to about 4 mm, or up to about 5 mm, or up to about 7.5 mm, or up to about 10 mm, or up to about 15 mm, or up to about 20 mm, or up to about 25 mm, or up to about 30 mm); and resolving the spectroscopic data in order to characterize the targeted tissue.

The targeted tissue can be cardiac tissue. Methods described herein are particularly applicable to characterizing cardiac tissue within a blood-filled, beating heart. Characterizing the targeted tissue may include detecting, measuring, or monitoring one or more of fibrotic tissue, allograft acceptance or rejection, myocarditis, amyloidosis, other cardiomyopathy, or one or more tissue parameters such as nuclear density. A method may include determining a volume fraction of constituents of targeted tissue and/or spatial distribution of the targeted tissue within the heart.

Some embodiments may further include characterizing tissue at multiple target locations to obtain one or more characterized data points; at each location, operating the tissue characterization probe to determine the location of the probe tip within the three-dimensional anatomical working space; associating each characterized data point with its corresponding determined location within the anatomical working space; and based on the characterized data points and their corresponding locations, generating a three-dimensional map of the anatomical working space. Additional details regarding such methods are described in more detail in PCT/US2018/016314 (published as WO2018144648A1), the entirety of which is incorporated herein by this reference.

Analysis of LSS Spectra Using Machine Learning

In the methods described herein, the step of resolving spectroscopic data in order to characterize the targeted tissue may include the use of one or more machine learning techniques. The machine learning technique(s) can include supervised or unsupervised techniques.

In one embodiment, an unsupervised machine learning technique utilized to resolve spectral data includes cluster analysis. The cluster analysis may apply a dimensionality reduction of spectra via principal component analysis (PCA). Euclidian distance can be used to generate similarity between nodes of first and second principal components of the spectra, and eigenvalues of the spectral cluster can indicate the number of groups into which sample data fall into. Additional details related to the use of spectral clustering for resolving spectral data for tissue characterization are included in the Examples section.

In another embodiment, a supervised machine learning technique utilized to resolve spectral data includes use of a convolutional neural network (CNN). The CNN may be trained to classify spectra into a selected number of groups/categories. The CNN may be trained using various approaches known in the art. One particularly useful training approach is the N−1 approach. For example, multiple CNNs (each with the same topology) are trained on a data set that includes all spectra from the data set except for one sample. Each data set omits a different sample such that the number of training data sets are equal to the number of samples, and each CNN of the multiple CNNs are trained on a different data set, depending on which sample was omitted.

CNNs may be trained for a set number of epochs and/or until a threshold level of loss is achieved. The CNNs can then be tested on the spectra omitted from their respective training set. One or more optimal CNNs may then be selected for use in characterization and/or for further training. The CNN may also be trained according to different spectra wavelength subgroupings in order to determine if there are dependencies of the CNN to particular wavelength ranges.

Pre-processing of spectra data prior to characterization and/or training can include various filtering steps and/or normalization (e.g., intensity normalization) steps. Other spectral data processing techniques known in the art may additionally or alternatively be utilized.

EXAMPLES

Tissue Characterization Functions

Experimental tissue stacks were used to test a tissue characterization probe. Thin tissue sections (200 µm thick) of myocardium or aortic tissue were placed on top of one another. Construct height was limited to up to 8 section layers (1.6 mm). Substrate layers were made using ventricular free wall myocardium from formalin-fixed adult canine heart, based on the rationale that the heart is mostly myocardium and the ventricles are largely free of fibrotic infiltrates. This also allowed for the investigation of tissue anisotropy. The target tissue was made from tissue from the ascending aorta and aortic arch of fixed adult canine hearts, based on the rationale that the aorta is composed of approximately 50% elastin and collagen by weight, and is readily accessible and identifiable in vivo.

To test depth sensitivity of the tissue characterization probe, two sections of the target tissue were sequentially lowered within the tissue stack to determine the depth at which the system was able to detect structures. The tissue detection probe has beneficially been capable of accurately detecting target tissue at depths of about 1.5 mm to 2 mm, and is expected to be capable of detecting target tissue at depths of up to about 4 mm through in at least some circumstances. The overall accuracy for depth detection, in this experimental setup, was approximately 95.45±3.99%.

Testing was also conducted to determine the sensitivity of the tissue characterization probe to detecting the volume fraction of fibrotic tissue, which is an important indicator of the functional ability of the tissue. Different volume fractions of fibrotic tissue within the overall stack were tested by varying the relative percentage of fibrotic tissue in a construct by 12.5% (i.e., one 200 μm section), until the entire volume faction of the construct was fibrotic tissue. Although it was initially expected that there may be some "masking" effects of upper layers of target tissue hiding lower layers, the overall average accuracy of the tissue characterization probe in determining the volume fraction of fibrotic tissue was beneficially high, at approximately 80.56±2.12%.

Testing was also conducted to describe mixed/permuted sections where the total volume fraction of aortic sections was 50%. Although it was initially expected that such "sandwiched" and/or mixed/embedded tissues would be difficult for the system to accurately characterize, the tissue characterization probe was able to accurately characterize such mixed/embedded tissues with a high accuracy of approximately 84.25±1.88%.

Exploratory measures were also taken in whole canine hearts (n=2) by acquiring spectra from several different locations (such as right atria, atrioventricular node, septal RA along the tendon of Todaro, joint of the septal leaf of tricuspid valve, aorta, ventricular wall, and sinoatrial node). The tissue characterization probe provided accuracies of up to 95%.

Analysis of LSS Spectra Using Machine Learning
Spectroscopy of Cardiac Tissue:

An LSS system was used to gather spectra from ovine ventricular tissue. We obtained transmural tissue samples from the right ventricular (RV) and left ventricular (LV) free wall as well as the ventricular septum of formalin-fixed hearts from 18 animals with gestational ages ranging 4.3 to 56 months. Samples were examined using LSS to identify changes in ND. The LSS probe was positioned on the epicardial surface at multiple locations to gather 20 spectra for all samples. Spectral acquisition occurred at 5 Hz. Spectra from the tissue samples were recorded at a resolution of 0.6 nm in the wavelength range of 500-1100 nm.

Raw spectra displayed a high degree of variability in intensity within samples and in-between samples. After normalization to their respective means, spectra from an individual sample exhibited a high correlation with the other spectra from the same sample ($R^2 \geq 0.999$). Differences between spectra from different samples were subtle ($R^2 = 0.996 \pm 0.002$).

Figure 6:
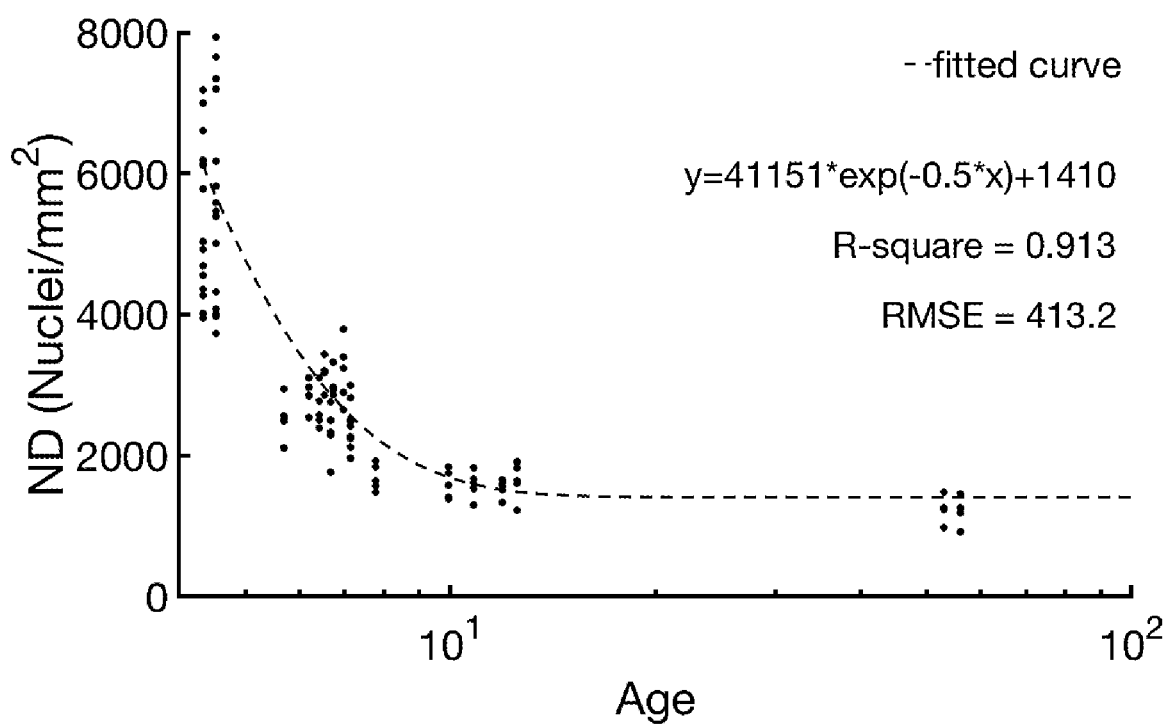
FIG. 6 illustrates counting of cell nuclei in cardiac tissue, showing a scatterplot and regression fit of measured NDs relative to age.

Histology:

Tissue samples were sectioned within the probed region at the center of each sample. Sections of 100 μm thickness perpendicular to the epicardial surface and parallel to the transmural plane of the heart wall were cut. After sectioning, glycoconjugates of the extracellular matrix and glycoproteins of cell membranes were labeled using wheat germ agglutinin (WGA) conjugated to a fluorophore. Cell nuclei were stained with 1 μM 6-diamidino-2-phenyindole (DAPI). ND was calculated by dividing the number of detected nuclei by the overall tissue area. The average ND for each heart provided the ground truth for machine learning. The reduction of ND with age is summarized in FIG. 6.

Cluster Analysis:

Cluster analysis applied a dimensionality reduction of the spectra via principal components analysis (PCA). We applied the MATLAB function spectralcluster to identify clusters of spectra from preparations of different NDs. The function allows the selection of the data, the distance metric, and the number of desired groups. The Euclidian distance was used to generate a similarity graph between nodes of the first and second principal components of the spectra. Analysis of the eigenvalues from the spectral cluster function indicated the spectra fell into 5 distinct groups. The desired number of groups was therefore varied between 3 and 5.

Figure 7A:
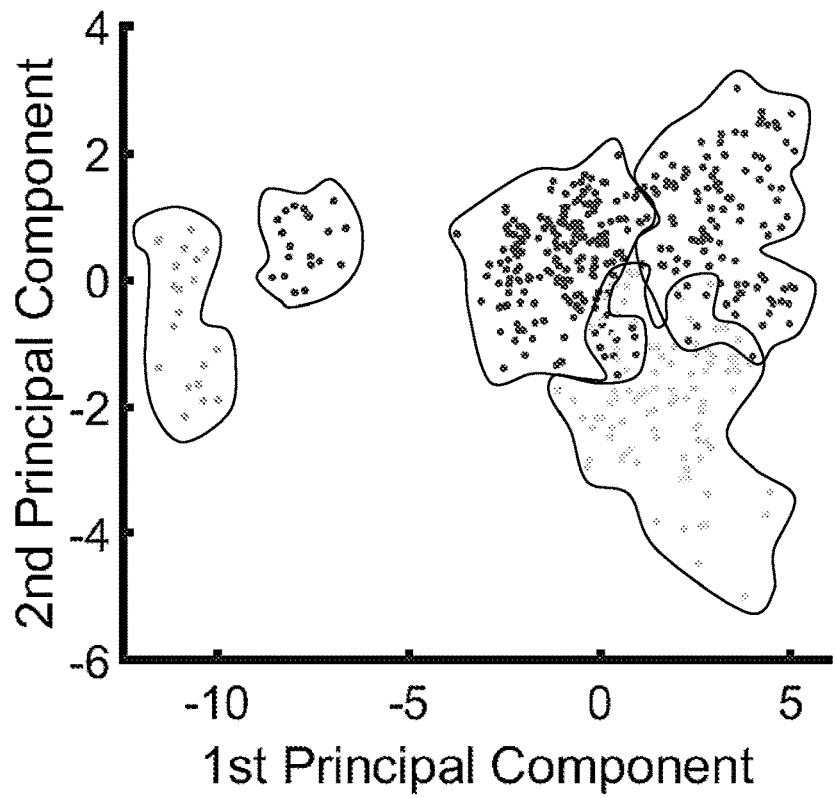
FIGS. 7A and 7B illustrate clustering of spectra measured from cardiac tissue, with FIG. 7A showing clusters identified in a principal component plot, and FIG. 7B showing that NDs of several identified clusters were different from other clusters (bracket connections mark clusters statistically different from each other at 5% confidence level)
Figure 7B:
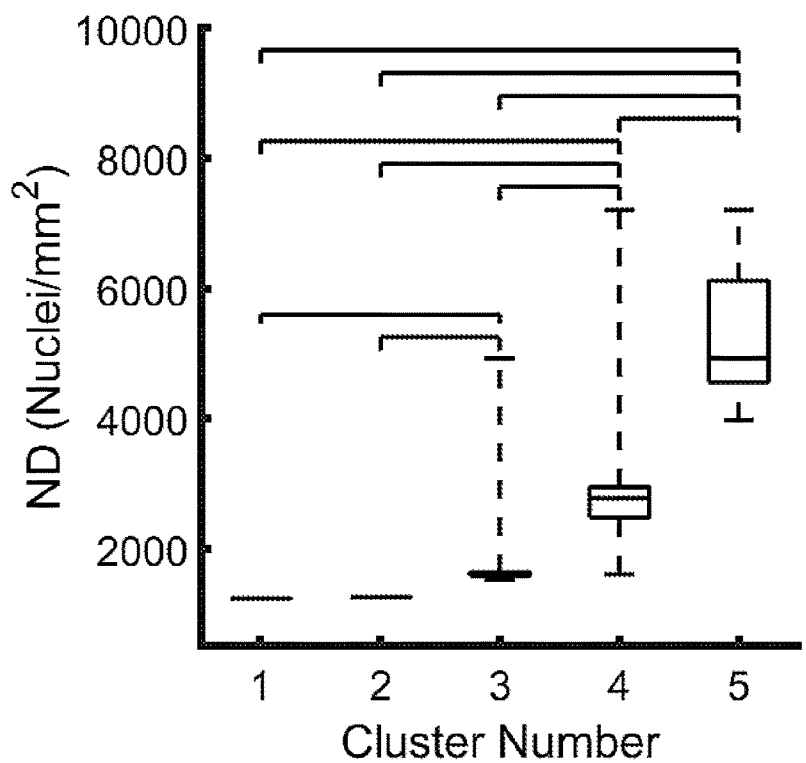

Approximately 95% of the variance of the spectra was described in the first two principal components of the spectra. Analysis of the eigenvalues indicated 5 distinct groups. A scatterplot of the first two principal components (FIG. 7A) illustrates these clusters. Cluster groups were labeled 1 to 5 with increasing ND. Analysis of variance revealed differences of ND for many of the clusters (FIG. 7B). Brackets connections mark clusters statistically different from each other at 5% confidence level.

Convolutional Neural Network:

We designed a CNN to classify the spectra into three groups of ND counts: up to 2000, 2000-3800, and above 3800 nuclei/mm². Loss values for the CNN were calculated by applying a softmax activation to the cross-entropy loss of the predicted class compared to the ground truth. The CNNs were systematically trained and validated using the N-1 approach. This approach entailed training 22 different CNNs with the same topology, each with a different training set that included all spectra from the entire dataset without the spectra gathered from one sample. Each of the 22 unique training datasets excluded the spectra from a different heart. Training of the CNNs was terminated after 2000 epochs or when the training loss did not decrease after more than 600 epochs. The CNN weights associated with the lowest loss value were saved and restored to the CNN to be used for testing. These CNNs were then tested on the spectra that were excluded from their respective training set.

To optimize CNN parameters, we systematically varied the batch size, learning rate, and convolution filter kernel size. The CNN configuration used for these parameter variations is described in Table 1. Seven batch sizes were tested which varied from 50 to 300. Ten different learning rates were tested that varied from 0.0001 to 0.015. Fifteen different convolution filter kernel sizes were tested which varied from 5 to 40. The full resolution spectra were then divided into three wavelength ranges: 500-700 nm, 700-900 nm, and 900-1100 nm. These partial spectra were used to train the CNN to determine the dependencies of the classification on specific wavelengths.

TABLE 1

CNN Configuration

| Level | Layer Type | Parameters |
|---|---|---|
| 1, 4, 7 | Convolution | Filter numbers: 8, 10, and 12 respectively<br>Kernel size: 18<br>Stride: 1<br>First layer input size: 7174 |
| 2, 5, 8 | ReLU | Rectified linear unit activation layer |
| 3, 6, 9 | Max Pooling | Pool size: 2<br>Stride: 0<br>Padding: none |
| 10 | Softmax | Exponential activation layer for multi-class classification |

Figure 8:
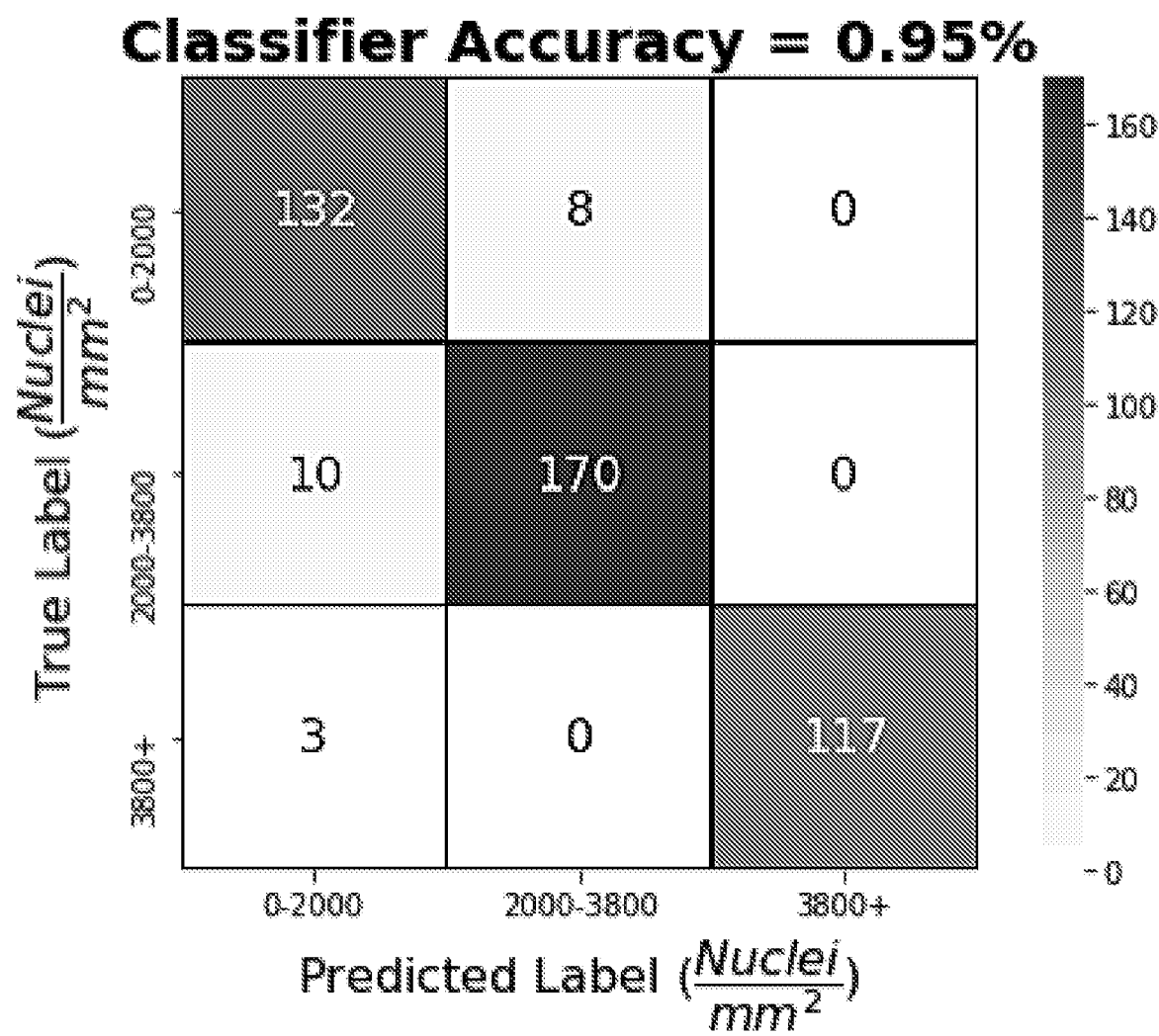
FIG. 8 illustrates a confusion matrix of aggregated CNN predictions of NDs from spectra, showing that classification of spectra was effective.

Parameter optimization yielded a kernel size of 20, a batch size of 100, and a learning rate of 0.003. The training of the CNN using the N−1 approach resulted in an accuracy of 95.23±12.20%. The confusion matrix of the CNN predictions is shown in FIG. 8. Training CNNs on different spectral wavelength ranges resulted in accuracies of 90.23±21.56%, 58.86±36.02%, and 81.59±34.52% for the 500-700 nm, 700-900 nm, and 900-1100 nm wavelength ranges, respectively. These results indicate that prediction of ND depends more on the low (500-700 nm) and high (900-100 nm) wavelength ranges than the mid (700-900 nm) range.

ADDITIONAL EMBODIMENTS

The following Embodiments are presented as examples. It will be appreciated that Embodiments may include properties, features (e.g., ingredients, components, members, elements, parts, and/or portions) described in other Embodiments. Accordingly, although certain features are recited in these the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

Embodiment 1: A tissue characterization probe, comprising: an elongate member having a proximal end and a distal end; a plurality of distal probe tips disposed at or near the distal end of the elongate member to form a multi-arm arrangement; a plurality of illumination fibers extending at least partially through the elongate member, each illumination fiber extending to a respective probe tip of the multi-arm arrangement such that each probe tip includes at least one illumination fiber; and a plurality of detection fibers extending at least partially through the elongate member, each detection fiber extending to a respective probe tip of the multi-arm arrangement such that each probe tip includes at least one detection fiber.

Embodiment 2: The tissue characterization probe of Embodiment 1, wherein the probe is configured to be introduced through a lumen or working channel of a catheter, guidable catheter, steerable sheath or working channel of an endoscope, and extends beyond the tip of catheter, sheath or working channel.

Embodiment 3: A tissue characterization system, comprising: a tissue characterization probe as in Embodiment 1 or Embodiment 2; a light source operatively coupled to the illumination fiber; and one or more spectrometers operatively coupled to the detection fibers.

Embodiment 4: The tissue characterization system of Embodiment 3, wherein the system is configured to characterize tissue within a depth greater than about 100 μm, such as up to about 1 mm, 1.5 mm, 2 mm, 2.5 mm, 3 mm, 3.5 mm, 4 mm, 5 mm, 7.5 mm, 10 mm, 15 mm, 20 mm, 25 mm, or 30 mm.

Embodiment 5: The tissue characterization system of Embodiment 3 or Embodiment 4, wherein the system is configured to characterize structurally anisotropic tissues such as cardiac tissues, optionally in a manner that reduces effects of rotation of the probe tip on the measured spectra.

Embodiment 6: A tissue characterization probe, comprising: an elongate member having a proximal end and a distal end; a distal probe tip disposed at the distal end of the elongate member; an illumination fiber extending at least partially through the elongate member to the probe tip and configured to, the illumination fiber defining an illumination axis; and a plurality of detection fibers extending at least partially through the elongate member to the probe tip and configured to receive light scattered from the targeted tissue, wherein a first set of detection fibers is substantially disposed along a first detection line, the first detection line being orthogonal to the illumination axis, and wherein a second set of detection fibers is substantially disposed along a second detection line, the second detection line being orthogonal to the illumination axis and being transverse to the first detection line.

Embodiment 7: The tissue characterization probe of Embodiment 6, wherein the probe is configured to be introduced through a lumen or working channel of a catheter, guidable catheter, steerable sheath or working channel of an endoscope, and extends beyond the tip of catheter, sheath or working channel.

Embodiment 8: The tissue characterization probe of Embodiment 6 or Embodiment 7, wherein each detection fiber is radially offset from its respective detection line by no more than about 30 degrees, or no more than about 25 degrees, or no more than about 20 degrees, or no more than about 15 degrees, or no more than about 10 degrees, or no more than about 5 degrees.

Embodiment 9: The tissue characterization probe of any one of Embodiments 6-8, wherein the first detection line and second detection line cross each other at the illumination axis to form a transverse angle of about 30° to about 150°, or about 45° to about 135°, or about 60° to about 120°, or about 75° to about 105°.

Embodiment 10: The tissue characterization probe of any one of Embodiments 6-9, wherein the second detection line is orthogonal to the first detection line.

Embodiment 11: The tissue characterization probe of any one of Embodiments 6-10, wherein the first set of detection fibers includes at least two detection fibers.

Embodiment 12: The tissue characterization probe of any one of Embodiments 6-11, wherein the second set of detection fibers includes at least two detection fibers.

Embodiment 13: The tissue characterization probe of any one of Embodiments 6-12, wherein the first set of detection fibers, the second set of detection fibers, or both are substantially adjacent the illumination fiber.

Embodiment 14: The tissue characterization probe of any one of Embodiments 6-12, wherein the detection fibers are spaced apart from the illumination fiber.

Embodiment 15: The tissue characterization probe of Embodiment 14, wherein the detection fibers are spaced apart from each other.

Embodiment 16: The tissue characterization probe of any one of Embodiments 6-15, further comprising a support wire extending at least partially through the elongate member to the probe tip and configured to increase bending stiffness of the probe tip.

Embodiment 17: The tissue characterization probe of any one of Embodiments 6-15, further comprising a support wire extending at least partially through the elongate member to the probe tip and configured to form a bend in the distal end of the probe tip.

Embodiment 18: The tissue characterization probe of Embodiment 16 or Embodiment 17, wherein the support wire has a quadrilateral cross-sectional shape.

Embodiment 19: The tissue characterization probe of Embodiment 18, wherein the support wire has a rectangular cross-sectional shape.

Embodiment 20: The tissue characterization probe of any one of Embodiments 6-19, wherein the tissue characterization probe, or multiple such tissue characterization probes, is/are incorporated into a multi-arm tissue characterization probe as in Embodiment 1 or Embodiment 2.

Embodiment 21: The tissue characterization probe of any one of Embodiments 1-20, wherein the probe further comprises one or more of an imaging assembly configured to provide microstructure imaging of targeted tissue, a localization assembly configured to provide location information of the distal tip within a three-dimensional anatomical working space, and/or a treatment assembly having one or more treatment components disposed at the distal tip for treating targeted tissue.

Embodiment 22: The tissue characterization probe of Embodiment 21, wherein the localization assembly comprises one or more electrodes, magnetic, optical, or other localization components to provide means for localization of the distal tip.

Embodiment 23: A tissue characterization system, comprising: a tissue characterization probe as in any one of Embodiments 6-22; a light source operatively coupled to the illumination fiber; and one or more spectrometers operatively coupled to the detection fibers.

Embodiment 24: The tissue characterization system of Embodiment 23, wherein the probe is configured to characterize tissue within a depth greater than about 100 μm, such as up to about 1 mm, 1.5 mm, 2 mm, 2.5 mm, 3 mm, 3.5 mm, 4 mm, 5 mm, 7.5 mm, 10 mm, 15 mm, 20 mm, 25 mm, or 30 mm.

Embodiment 25: A method of characterizing tissue, comprising: providing a tissue characterization system; directing the distal probe tip to a targeted anatomical location; at the targeted anatomical location, operating the tissue characterization probe to obtain spectra within depths greater than about 100 μm, such as up to about 1 mm, 1.5 mm, 2 mm, 2.5 mm, 3 mm, 3.5 mm, 4 mm, 5 mm, 7.5 mm, 10 mm, 15 mm, 20 mm, 25 mm, or 30 mm; and resolving the spectra in order to characterize the targeted tissue.

Embodiment 26: The method of Embodiment 25, wherein the targeted tissue is cardiac tissue.

Embodiment 27: The method of Embodiment 26, wherein the targeted anatomical location is a blood-filled, beating heart.

Embodiment 28: The method of any one of Embodiments 25-27, wherein the tissue characterization system is a system as in any one of Embodiments 3-5 or 23-24.

Embodiment 29: The method of any one of Embodiments 25-28, wherein characterizing the targeted tissue comprises detecting, measuring, or monitoring one or more of fibrosis, allograft acceptance or rejection, myocarditis, amyloidosis, hypertrophy, to or nuclear density.

Embodiment 30: The method of any one of Embodiments 25-29, wherein characterizing the targeted tissue comprises determining a volume fraction of constituents of the targeted tissue and/or spatial distribution of constituents of the targeted tissue within the heart.

Embodiment 31: The method of any one of Embodiments 25-30, further comprising: characterizing tissue at multiple target locations and obtaining one or more data points of the characterized tissue; at each location of data acquisition, determine the location of the probe tip within the three-dimensional anatomical working space; associating each data point with its corresponding determined location within the anatomical working space; and based on the data points and their corresponding locations, generating a three-dimensional map of tissue microstructure.

Embodiment 32: The method of Embodiment 31, wherein the three-dimensional map is a fibrosis map.

Embodiment 33: The method of Embodiment 31 or Embodiment 32, wherein the step of characterizing tissue at multiple target locations includes simultaneous characterization of tissues at the multiple target locations.

Embodiment 34: The method of any one of Embodiments 25-33, wherein the step of resolving spectra in order to characterize the targeted tissue comprises utilizing an unsupervised machine learning technique.

Embodiment 35: The method of Embodiment 34, wherein the unsupervised machine learning technique includes cluster analysis.

Embodiment 36: The method of Embodiment 35, wherein the cluster analysis includes dimensionality reduction of spectra via principal component analysis (PCA).

Embodiment 37: The method of Embodiment 36, wherein the cluster analysis includes measuring similarity from at least the first and second principal components of the spectra.

Embodiment 38: The method of Embodiment 37, wherein similarity from at least the first and second principal components of the spectra is based on Euclidean distance.

Embodiment 39: The method of any one of Embodiments 25-33, wherein the step of resolving spectra in order to characterize the targeted tissue comprises utilizing a supervised machine learning technique.

Embodiment 40: The method of Embodiment 39, wherein the supervised machine learning technique includes a convolutional neural network (CNN).

Embodiment 41: The method of Embodiment 40, wherein the CNN is trained and tested using data from a set of prior measurements of scattering in tissues.

Embodiment 42: The method of Embodiment 40 or Embodiment 41, wherein a batch size for training of the CNN varies from 50 to 300.

Embodiment 43: The method of any one of Embodiments 40-42, wherein a learning rate of the CNN varies from 0.0001 to 0.015.

Embodiment 44: The method of any one of Embodiments 40-43, wherein a convolution filter kernel size of the CNN varies from 5 to 40.

Embodiment 45: The method of any one of Embodiments 40-44, wherein the CNN is trained from spectra within specific wavelength ranges and/or is trained with reduced sampling.

CONCLUSION

While certain embodiments of the present disclosure have been described in detail, with reference to specific configurations, parameters, components, elements, etcetera, the descriptions are illustrative and are not to be construed as limiting the scope of the claimed invention. Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims. It will also be noted that, as used in this specification and the appended claims, the singular forms "a," "an" and "the" do not exclude plural referents unless the context clearly dictates otherwise.

Thus, for example, an embodiment referencing a singular referent (e.g., "widget") may also include two or more such referents.

The invention claimed is:

1. A tissue characterization probe, comprising:
an elongate member having a proximal end and a distal end;
a plurality of distal probe tips disposed at or near the distal end of the elongate member to form a multi-arm arrangement;
a plurality of illumination fibers extending at least partially through the elongate member, each illumination fiber extending to a respective probe tip of the multi-arm arrangement such that each probe tip includes at least one illumination fiber; and
a plurality of detection fibers extending at least partially through the elongate member, each detection fiber extending to a respective probe tip of the multi-arm arrangement such that each probe tip includes at least one detection fiber,
wherein the probe is configured to be introduced through a lumen or working channel of a catheter, guidable catheter, steerable sheath or working channel of an endoscope, and is extendable beyond the tip of catheter, sheath or working channel.

2. A tissue characterization system, comprising:
(i) a tissue characterization probe that comprises:
an elongate member having a proximal end and a distal end;
a plurality of distal probe tips disposed at or near the distal end of the elongate member to form a multi-arm arrangement;
a plurality of illumination fibers extending at least partially through the elongate member, each illumination fiber extending to a respective probe tip of the multi-arm arrangement such that each probe tip includes at least one illumination fiber; and
a plurality of detection fibers extending at least partially through the elongate member, each detection fiber extending to a respective probe tip of the multi-arm arrangement such that each probe tip includes at least one detection fiber;
(ii) a light source operatively coupled to the illumination fiber; and
(iii) one or more spectrometers operatively coupled to the detection fibers.

3. The tissue characterization system of claim 2, wherein the system is configured to characterize tissue within a depth greater than about 100 µm and up to about 30 mm.

4. The tissue characterization system of claim 2, wherein the system is configured to characterize structurally anisotropic tissues.

5. A tissue characterization probe, comprising:
an elongate member having a proximal end and a distal end;
a distal probe tip disposed at the distal end of the elongate member;
an illumination fiber extending at least partially through the elongate member to the probe tip and configured to direct light toward target tissue, the illumination fiber defining an illumination axis; and
a plurality of detection fibers extending at least partially through the elongate member to the probe tip and configured to receive light scattered from the targeted tissue,
wherein a first set of detection fibers is substantially disposed along a first detection line, the first detection line being orthogonal to the illumination axis,
wherein a second set of detection fibers is substantially disposed along a second detection line, the second detection line being orthogonal to the illumination axis and being transverse to the first detection line,
wherein the probe is configured to be introduced through a lumen or working channel of a catheter, guidable catheter, steerable sheath or working channel of an endoscope, and is extendable beyond the tip of catheter, sheath or working channel.

6. The tissue characterization probe of claim 5, wherein each detection fiber is radially offset from its respective detection line by no more than about 30 degrees.

7. The tissue characterization probe of claim 5, wherein the first detection line and second detection line cross each other at the illumination axis to form a transverse angle of about 30° to about 150°.

8. The tissue characterization probe of claim 5, wherein the second detection line is orthogonal to the first detection line.

9. The tissue characterization probe of claim 5, wherein the first set of detection fibers includes at least two detection fibers.

10. The tissue characterization probe of claim 5, wherein the second set of detection fibers includes at least two detection fibers.

11. The tissue characterization probe of claim 5, wherein the first set of detection fibers, the second set of detection fibers, or both are substantially adjacent the illumination fiber.

12. The tissue characterization probe of claim 5, wherein the detection fibers are spaced apart from the illumination fiber.

13. The tissue characterization probe of claim 12, wherein the detection fibers are spaced apart from each other.

14. The tissue characterization probe of claim 5, further comprising a support wire extending at least partially through the elongate member to the probe tip and configured to increase bending stiffness of the probe tip.

15. The tissue characterization probe of claim 5, further comprising a support wire extending at least partially through the elongate member to the probe tip and configured to form a bend in the distal end of the probe tip.

16. The tissue characterization probe of claim 14, wherein the support wire has a quadrilateral cross-sectional shape.

17. The tissue characterization probe of claim 16, wherein the support wire has a rectangular cross-sectional shape.

18. The tissue characterization probe of claim 1, wherein the probe further comprises one or more of an imaging assembly configured to provide microstructure imaging of targeted tissue, a localization assembly configured to provide location information of the distal tip within a three-dimensional anatomical working space, and/or a treatment assembly having one or more treatment components disposed at the distal tip for treating targeted tissue.

19. The tissue characterization probe of claim 18, wherein the localization assembly comprises one or more electrodes, magnetic, optical, or other localization components to provide means for localization of the distal tip.

20. A tissue characterization system, comprising:
(i) a tissue characterization probe comprising:
an elongate member having a proximal end and a distal end;
a distal probe tip disposed at the distal end of the elongate member;
an illumination fiber extending at least partially through the elongate member to the probe tip and configured to, the illumination fiber defining an illumination axis; and
a plurality of detection fibers extending at least partially through the elongate member to the probe tip and configured to receive light scattered from the targeted tissue,
wherein a first set of detection fibers is substantially disposed along a first detection line, the first detection line being orthogonal to the illumination axis, and
wherein a second set of detection fibers is substantially disposed along a second detection line, the second detection line being orthogonal to the illumination axis and being transverse to the first detection line,
(ii) a light source operatively coupled to the illumination fiber; and
(iii) one or more spectrometers operatively coupled to the detection fibers.

21. The tissue characterization system of claim 20, wherein the probe is configured to characterize tissue within a depth greater than about 100 μm and up to about 30 mm.

22. A method of characterizing tissue, comprising:
providing a tissue characterization system;
directing the distal probe tip to a targeted anatomical location;
at the targeted anatomical location, operating the tissue characterization probe to obtain spectra within depths greater than about 100 μm and up to about 30 mm; and
resolving the spectra in order to characterize the targeted tissue,
wherein the targeted tissue is cardiac tissue.

23. The method of claim 22, wherein the targeted anatomical location is a blood-filled, beating heart.

24. The method of claim 22, wherein characterizing the targeted tissue comprises detecting, measuring, or monitoring one or more of fibrosis, allograft acceptance or rejection, myocarditis, amyloidosis, hypertrophy, or nuclear density.

25. The method of claim 22, wherein characterizing the targeted tissue comprises determining a volume fraction of constituents of the targeted tissue and/or spatial distribution of constituents of the targeted tissue within the heart.

26. The method of claim 22, further comprising:
characterizing tissue at multiple target locations and obtaining one or more data points of the characterized tissue;
at each location of data acquisition, determine the location of the probe tip within the three-dimensional anatomical working space;
associating each data point with its corresponding determined location within the anatomical working space; and
based on the data points and their corresponding locations, generating a three-dimensional map of tissue microstructure.

27. The method of claim 26, wherein the three-dimensional map is a fibrosis map.

28. The method of claim 26, wherein the step of characterizing tissue at multiple target locations includes simultaneous characterization of tissues at the multiple target locations.

29. The method of claim 22, wherein the step of resolving spectra in order to characterize the targeted tissue comprises utilizing an unsupervised machine learning technique.

30. The method of claim 29, wherein the unsupervised machine learning technique includes cluster analysis.

31. The method of claim 30, wherein the cluster analysis includes dimensionality reduction of spectra via principal component analysis (PCA).

32. The method of claim 31, wherein the cluster analysis includes measuring similarity from at least the first and second principal components of the spectra.

33. The method of claim 32, wherein similarity from at least the first and second principal components of the spectra is based on Euclidean distance.

34. The method of claim 22, wherein the step of resolving spectra in order to characterize the targeted tissue comprises utilizing a supervised machine learning technique.

35. The method of claim 34, wherein the supervised machine learning technique includes a convolutional neural network (CNN).

36. The method of claim 35, wherein the CNN is trained and tested using data from a set of prior measurements of scattering in tissues.

37. The method of claim 35, wherein a batch size for training of the CNN varies from 50 to 300.

38. The method of claim 35, wherein a learning rate of the CNN varies from 0.0001 to 0.015.

39. The method of claim 35, wherein a convolution filter kernel size of the CNN varies from 5 to 40.

40. The method of claim 35, wherein the CNN is trained from spectra within specific wavelength ranges and/or is trained with reduced sampling.

41. A tissue characterization probe, comprising:
an elongate member having a proximal end and a distal end;
a distal probe tip disposed at the distal end of the elongate member;
an illumination fiber extending at least partially through the elongate member to the probe tip and configured to direct light toward target tissue, the illumination fiber defining an illumination axis; and
a plurality of detection fibers extending at least partially through the elongate member to the probe tip and configured to receive light scattered from the targeted tissue, wherein a first set of detection fibers is substantially disposed along a first detection line, the first detection line being orthogonal to the illumination axis, wherein a second set of detection fibers is substantially disposed along a second detection line, the second detection line being orthogonal to the illumination axis and being transverse to the first detection line, and wherein each detection fiber is radially offset from its respective detection line by no more than about 30 degrees.

42. A tissue characterization probe, comprising:

an elongate member having a proximal end and a distal end;

a distal probe tip disposed at the distal end of the elongate member;

an illumination fiber extending at least partially through the elongate member to the probe tip and configured to direct light toward target tissue, the illumination fiber defining an illumination axis; and a plurality of detection fibers extending at least partially through the elongate member to the probe tip and configured to receive light scattered from the targeted tissue, wherein a first set of detection fibers is substantially disposed along a first detection line, the first detection line being orthogonal to the illumination axis, wherein a second set of detection fibers is substantially disposed along a second detection line, the second detection line being orthogonal to the illumination axis and being transverse to the first detection line, and wherein the first detection line and second detection line cross each other at the illumination axis to form a transverse angle of about 30° to about 150°.

43. A tissue characterization probe, comprising:

an elongate member having a proximal end and a distal end;

a distal probe tip disposed at the distal end of the elongate member;

an illumination fiber extending at least partially through the elongate member to the probe tip and configured to direct light toward target tissue, the illumination fiber defining an illumination axis;

a plurality of detection fibers extending at least partially through the elongate member to the probe tip and configured to receive light scattered from the targeted tissue; and a support wire extending at least partially through the elongate member to the probe tip and configured to (i) increase bending stiffness of the probe tip, (ii) form a bend in the distal end of the probe tip, or both, wherein a first set of detection fibers is substantially disposed along a first detection line, the first detection line being orthogonal to the illumination axis, and wherein a second set of detection fibers is substantially disposed along a second detection line, the second detection line being orthogonal to the illumination axis and being transverse to the first detection line.

44. A method of characterizing tissue, comprising:

providing a tissue characterization system;

directing the distal probe tip to a targeted anatomical location;

at the targeted anatomical location, operating the tissue characterization probe to obtain spectra within depths greater than about 100 µm and up to about 30 mm; and resolving the spectra in order to characterize the targeted tissue, wherein the step of resolving spectra in order to characterize the targeted tissue comprises utilizing a supervised or an unsupervised machine learning technique.

* * * * *